United States Patent [19]

Bousquet et al.

[11] Patent Number: 5,262,561
[45] Date of Patent: Nov. 16, 1993

[54] PROCESS FOR PREPARING (E)-2-PROPYL-2-PENTENOIC ACID AND INTERMEDIATE COMPOUNDS

[75] Inventors: André Bousquet; Alain Heymes, both of Sisteron, France

[73] Assignee: Elf Sanofi, Paris, France

[21] Appl. No.: 850,910

[22] Filed: Mar. 13, 1992

[30] Foreign Application Priority Data

Mar. 15, 1991 [FR] France .................. 91 03219

[51] Int. Cl.$^5$ .................................. C07C 67/30
[52] U.S. Cl. ........................... 560/213; 560/226
[58] Field of Search ............................ 560/213

[56] References Cited

FOREIGN PATENT DOCUMENTS 3718801 12/1988 Fed. Rep. of Germany .

OTHER PUBLICATIONS

Chemical Abstracts, vol. 87, No. 11, Sep. 12, 1977.

Primary Examiner—Paul J. Killos
Attorney, Agent, or Firm—Wegner, Cantor, Mueller & Player

[57] ABSTRACT

Composition consisting of a mixture of (E) and (Z) isomers of esters of general formula:

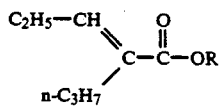

in which R represents a $C_1$–$C_4$ alkyl radical, containing at least 85% of (E) isomer.

A process for preparing such a composition. The use of such a composition for preparing (E)-2-propyl-2-pentenoic acid of formula:

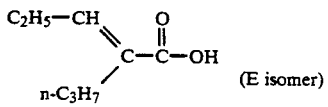

and also its pharmaceutically acceptable salts.

37 Claims, 1 Drawing Sheet

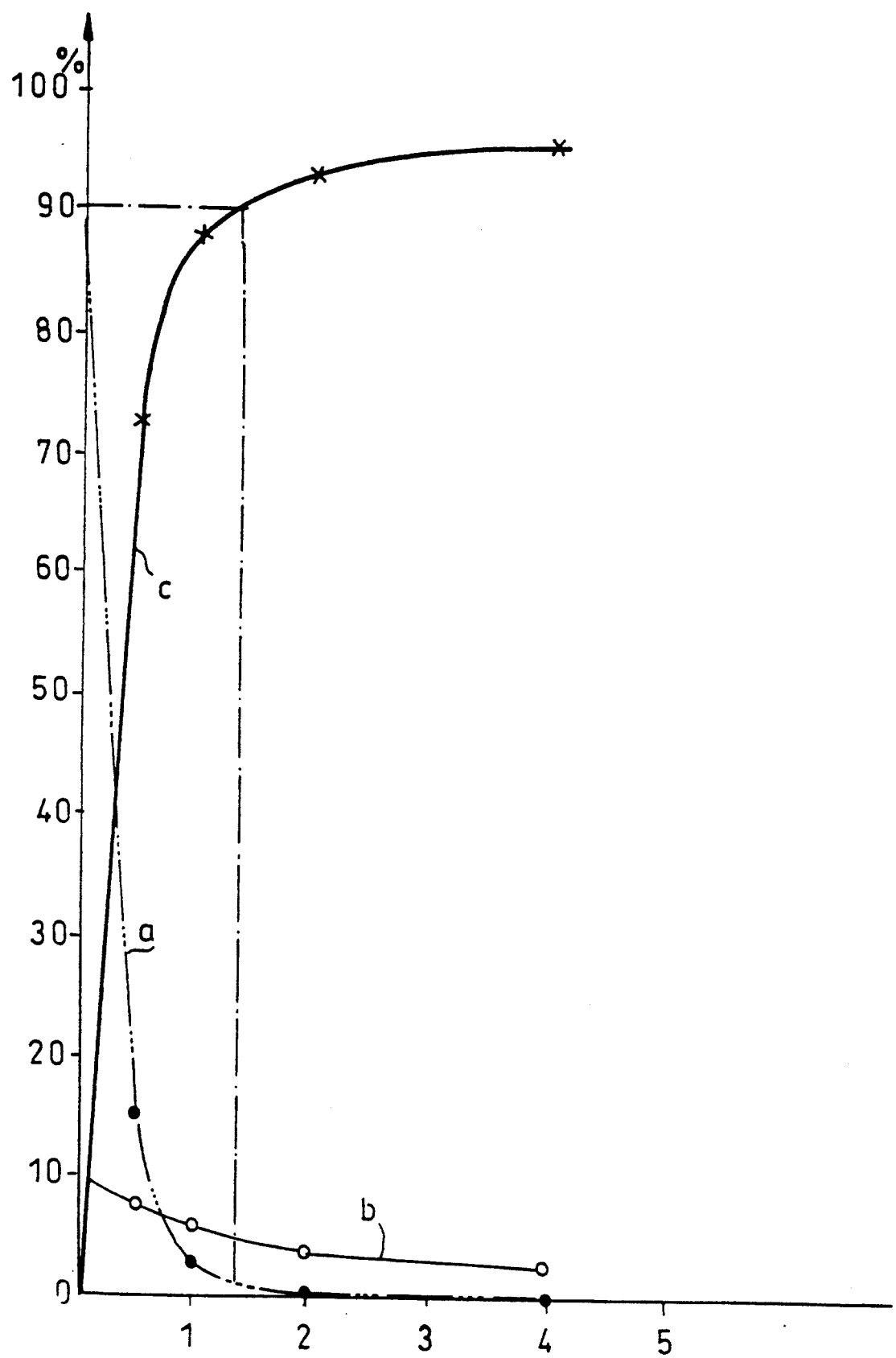

PROCESS FOR PREPARING (E)-2-PROPYL-2-PENTENOIC ACID AND INTERMEDIATE COMPOUNDS

The present invention relates, generally speaking, to new compositions consisting of mixtures of isomers of ethylenic esters, to a process for preparing them and also to their use as synthesis intermediates.

In particular, the invention relates to compositions consisting of mixtures of (E) and (Z) isomers of ethylenic esters of general formula:

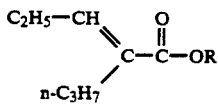    I in which R represents a $C_1-C_4$ alkyl radical, preferably an ethyl radical, these mixtures containing at least 85% of (E) isomer.

The compositions consisting of mixtures of (E) and (Z) isomers of esters of formula I containing at least 90% of (E) isomer constitute preferred compositions of the invention, especially the composition consisting of a mixture containing 90% of (E) isomer.

The compositions consisting of mixtures of (E) and (Z) isomers of esters of formula I have proved especially useful as intermediate products, in particular for the preparation of (E)-2-propyl-2-pentenoic acid of formula:

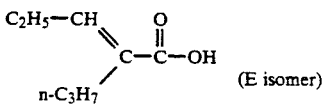 (E isomer)    Ia and also its pharmaceutically acceptable salts, especially the sodium salt.

This acid of formula Ia is a known product which has been described, in particular, in Arch. Pharm. 310 (5) pp. 394–403 (1977) and in J.A.C.S. 93, (17 pp. 4242–4247 (1971).

It is a metabolite of valproic acid, a compound known for its anticonvulsant properties and widely used in the treatment of epilepsy.

The acid of formula Ia also possesses a not insignificant anti-epileptic activity and a lower degree of teratogenicity then that of valproic acid.

Several processes for preparing (E)-2-propyl-2-pentenoic acid are already known.

However, most of them possess drawbacks such that their use cannot be validly envisaged for production at industrial level. In effect, these various processes involve:
   either dangerous reactants such as sodium cyanide, necessitating a fastidious implementation,
   or starting compounds which are relatively developed and difficult to obtain, such as 4-hydroxy-5-octanone,
   or a large number of steps with, at the end, a poor overall yield, of the order of 30%, coupled with a rather tedious implementation on account of the reactants used.

Processes exist, however, for preparing the (E)-2-propyl-2-pentenoic acid in question entailing a relatively limited number of steps and employing readily accessible reactants. However, these processes possess drawbacks, the greatest of which are characterised by a lack of selectivity in respect of the isomers of the 2-propyl-2-pentenoic acid formed (geometric and position isomers) and a difficulty in separation of these isomers, leading to rather poor overall yields.

In this connection, the process described in Arch. Pharm. 310 (1977) cited above may be mentioned, according to which process:

a) a dehydrohalogenation of ethyl 2-bromo-2-propylpentanoate is carried out under reflux by means of N,N-diethylaniline, and a purification by distillation (yield: 76.5%), b) the ester thereby obtained is saponified under reflux by means of 1.5M aqueous sodium hydroxide solution and in the presence of ethanol, the mixture is treated with sulphuric acid and the product is purified by fractional crystallisation in petroleum ether (yield: 25%). The overall yield of this process proves very low, namely of the order of 19% starting from the ethyl 2-bromo-2-propylpentanoate.

A modification of this method has been described in Patent Application EP-293,753, according to which the following are carried out:

a) dehydrohalogenation of ethyl 2-bromo-2-propylpentanoate by means of 1,4-diazabicyclo[2.2.2]octane in acetonitrile, the reaction taking place for 8 h at the refluxing temperature of the medium, to obtain, after concentration, a 77:23 mixture of (E) and (Z) isomers of ethyl 2-propyl-2-pentenoate [yield: 80%, equivalent to a 62% yield of (E) isomer], b) saponification of the mixture of isomers in question by means of 10 equivalents of sodium hydroxide in methanol and for 5 days at room temperature, followed by acidification of the medium to give a quantitative 80:20 crude mixture of (E)-2-propyl-2-pentenoic/2-propyl-3-pentenoic ($\Delta^3$ isomer) acid, and finally purification by distillation (yield not specified).

Consequently, the above process enables crude (E)-2-propyl-2-pentenoic acid to be obtained in a maximum yield of no more than 48%.

In addition, during the separation of the isomers formed in respect of 2-propyl-2-pentenoic acid, considerable problems may be expected, since it is pointed out in the patent application in question that the distillation to be carried out for the purification is exacting and must be performed by means of a powerful column.

The development of a process capable of being used at industrial level and enabling the acid of formula Ia to be prepared in pure form, that is to say free from isomers and in good yield, hence remains of major importance.

Now, it has been discovered, surprisingly, according to the invention, that the compositions consisting of mixtures of (E) and (Z) isomers of esters of formula I can give access to (E)-2-propyl-2-pentenoic acid and its pharmaceutically acceptable salts, in yields which are far greater than those provided by the prior processes and with an especially exceptional degree of purity.

These compositions have proved all the more advantageous for the fact that they can be prepared with ease and with large chemical yields.

In effect, it was found that the compositions of the invention may be obtained, in particular, by simply heating a 2-bromo-2-propylpentanoic ester in a polar aprotic solvent containing an amide group, such as N,N-dimethylformamide, a solvent which consequently proves capable of inducing a dehydrobromination reaction (elimination of HBr) in respect of this ester, in distinction to acetonitrile.

Consequently, the invention relates to compositions consisting of mixtures or (E) and (Z) isomers of esters of formula I, as new industrial products, which are useful, in particular, as synthesis intermediates, for example for the preparation of (E)-2-propyl-2-pentenoic acid and its pharmaceutically acceptable salts.

According to the invention, the compositions in question are prepared according to a process involving the following steps:

a) 2-n-propylpentanoic acid or valproic acid, of formula:

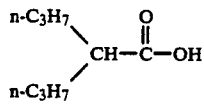

is treated in a polar solvent, first with thionyl chloride, then with bromine and finally with an alcohol of general formula:

R—OH    III in which R has the same meaning as above, the reactions taking place in an aprotic solvent such as dichloroethane, to obtain an α-bromo ester of general formula:

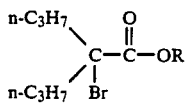

in which R has the same meaning as above, b) the ester thereby obtained is heated to a temperature of 30° C. to 130° C. in a polar aprotic solvent containing an amide group, and optionally in the presence of a tertiary amine, yielding a composition consisting of a mixture of (E) and (Z) isomers of formula I containing at least 85% of (E) isomer.

Preferably, an alcohol of formula III in which R represents an ethyl group, that is to say ethanol, and an α-bromo ester of formula IV in which R also represents an ethyl group, namely ethyl 2-bromo-2-propylpentanoate, are used.

As a polar aprotic solvent containing an amide group, N,N-dimethylformamide, N,N-dimethylacetamide or N-methylpyrrolidone is generally used.

N,N-dimethylformamide constitutes, however, a preferred solvent.

Furthermore, the heating of the ester of formula IV in the solvent as the sole dehydrobrominating agent is generally performed at a temperature of 90° C. to 130° C., and preferably at a temperature of the order of 100° C. to 125° C.

According to a variant of the above process for the preparation of the compositions of the invention, the heating of the ester of formula IV in the solvent in question is performed in the presence of a tertiary amine, generally a $C_1$-$C_4$ trialkylamine such as trimethylamine (TMA), triethylamine (TEA) or trimethylethylenediamine (TMEDA), or alternatively in the presence of 1,4-diazabicyclo[2.2.2]octane (DABCO).

The preferred solvent in this variant also is N,N-dimethylformamide.

Under these conditions, the treatment in question is performed in the presence of a maximum of 2 mol of tertiary amine per mole of ester of formula IV, and generally at a temperature of 30° C. to 100° C., for example at a temperature of 40° C. to 70° C., but preferably at a temperature of the order of 55° C.

As stated above, polar aprotic solvents containing an amide group, and in particular N,N-dimethylformamide, can act as dehydrobrominating agents, in distinction to acetonitrile.

In effect, comparative tests were performed, according to the working conditions of the invention, by heating 1 equivalent by weight of ethyl 2-bromo-2-propylpentanoate in 2 equivalents by volume of solvent, namely acetonitrile, N,N-dimethylformamide (DMF) or N,N-dimethylacetamide (DMAC), to 75° C. for 23 hours.

The results below state the percentage of ethyl 2-bromo-2-propylpentanoate converted to a mixture of (E) and (Z) isomers of ethyl 2-propyl-2-pentenoate, the percentage of each of the isomers obtained and also the ratio of these isomers in the mixture they form.

| Solvent | % conversion | isomers | | |
| --- | --- | --- | --- | --- |
| | | E (%) | Z (%) | E/Z |
| Acetonitrile | 0 | 0 | 0 | 0 |
| DMF | 24.2 | 20.5 | 2.5 | 89/11 |
| DMAC | 38 | 33.3 | 4.4 | 88.3/11.7 |

These results show that, all working conditions being identical, DMF and DMAC induce a dehydrobromination reaction of ethyl 2-propylpentanoate, in distinction to acetonitrile, so as to form a mixture of (E) and (Z) isomers of ethyl 2-propyl-2-pentenoate containing at least 85% of (E) isomer.

The compositions according to the invention, obtained according to the process of the invention, proved to be free of the corresponding 2-propyl-3-pentenoic esters.

In addition, their yield starting from the α-bromo ester of formula IV proved excellent.

As an example, compositions according to the invention could be obtained with chemical yields generally greater than 90% starting from ethyl 2-bromo-2-propylpentanoate, and sometimes greater than 95%.

As stated above, the compositions according to the invention may be validly used for the preparation of (E)-2-propyl-2-pentenoic acid of formula Ia.

Consequently, another subject of the invention relates to the preparation of the acid of formula Ia, by carrying out a process according to which a composition according to the invention, consisting of a mixture of (E) and (Z) isomers of esters of formula I containing at least 85% of (E) isomer, is saponified by means of an alkali metal hydroxide in an aqueous reaction medium containing an alcohol of formula III, and then acidifying the medium by means of a strong acid to obtain (E)-2-propyl-2-pentenoic acid.

The acid obtained according to this method possesses a high degree of purity, since its titer of pure (E) isomer is generally of the order of 95 to 96%.

Preferably, a composition consisting of a mixture of (E) and (Z) isomers of ethyl 2-propylpentanoate, and ethanol as the alcohol of formula III, are used.

The saponification generally takes place in the presence of 1 to 10 equivalents, and preferably 1 to 5 equivalents, of an alkali metal hydroxide, preferably sodium hydroxide.

This saponification reaction in general proceeds at a temperature ranging from room temperature to 100° C., for example at a temperature of 30° C. to 100° C.

In addition, this saponification reaction is performed in a reaction medium composed of an aqueous medium containing an alcohol of formula III, preferably 50 to 150% by volume, for example 100%, per volume of water and also, preferably, 2 to 10 mol/l of alkali metal hydroxide, for example 3 to 8 mol/l, and generally 1 to 5 mol of a composition of the invention, such as 1 to 3 mol/l and preferably 1.5 mol/l.

The acidification, for its part, is generally performed at a temperature of +20° C. to −10° C., and preferably at a temperature of 0° C. to −10° C.

According to this method, (E)-2-propyl-2-pentenoic acid may be obtained with an excellent chemical yield, namely of the order of 95% starting from the composition of the invention. In addition, the overall yield proves far greater than that obtained according to the prior techniques, since it is approximately 90% starting from the (E) isomer of formula I and of the order of 75% starting from the α-bromo derivative of formula IV.

Furthermore, the degree of purity of the acid of formula Ia thereby obtained proves very high, namely greater than 95%.

If necessary, the purification of this acid of formula Ia can be improved by one or more recrystallisations in an aqueous medium containing an alcohol of formula III, a medium similar to that defined above for the saponification.

Generally, a single recrystallisation suffices to obtain a product of very high purity, namely assaying at not less than 98% of (E) isomer [(Z) isomer <1.5% and $\Delta^3$ isomer <0.3%].

After purification, the yield of (E) isomer of 2-propyl-2-pentenoic acid is approximately 72% starting from the α-bromo ester of formula IV.

The preparation of the acid of formula Ia, by saponification starting from a composition consisting of a mixture of (E) and (Z) isomers of esters of formula I according to the invention, may be carried out according to a variant of the method described above.

This variant is based, in particular, on the demonstration of completely different kinetics of saponification of the (E) and (Z) isomers of the 2-propyl-2-pentenoic esters of formula I, since it was found that (E) isomer saponifies much more rapidly than the corresponding (Z) isomer. Consequently, advantage may be taken of this difference by controlling the degree of saponification in an effective manner so as to limit the conversion to a maximal mixture with respect to (E)-2-propyl-2-pentenoic acid salt and minimal mixture with respect to (Z)-2-propyl-2-pentenoic acid salt.

This variant of the method of saponification according to the invention proved especially effective when it was carried out starting from a composition consisting of a mixture of (E) and (Z) isomers of esters of formula I according to the invention.

According to the variant in question, (E)-2-propyl-2-pentenoic acid is prepared:

a) by saponifying a composition according to the invention, consisting of a mixture of (E) and (Z) isomers of ethylenic esters of formula I, to a degree of conversion of 90 to 92%, the saponification being performed by means of an alkali metal hydroxide in an aqueous reaction medium containing an alcohol of formula III, by extracting the unsaponified esters by means of a water-immiscible solvent, for example an ether, and by acidifying the aqueous reaction medium by means of a strong acid after extraction of the unsaponified esters, to obtain essentially (E)-2-propyl-2-pentenoic acid b) by purifying the 2-pentenoic acid obtained, by one or more crystallisations in water and in the presence of an alcohol of formula III, yielding (E)-2-propyl-2-pentenoic acid in especially pure form.

The saponification generally takes place in the presence of 2 to 10 equivalents, and preferably 5 equivalents, of an alkali metal hydroxide. Preferably, sodium hydroxide is used as the alkali metal hydroxide.

This saponification reaction in general proceeds at a temperature of 30° to 50° C., and preferably at a temperature of the order of 40° C., in a reaction medium composed of an aqueous medium containing an alcohol of formula III, preferably 50 to 150% by volume, for example 100%, per volume of water and also, preferably, 2 to 10 mol/l alkali metal hydroxide, for example 7.5 mol/l, and preferably 1 to 3 mol/l of a composition of esters of formula I according to the invention. The strong acid, for its part, is generally a hydracid such as hydrochloric acid.

The process thus described enables the acid of formula Ia to be obtained in yields in the region of 85% starting from the (E) ester of formula I, and of the order of 75% of repurified product calculated from the ester of formula IV. In addition, the pure product thereby obtained possesses a titer of (E)-2-propyl-2-pentenoic acid of greater than 98%, or even greater than 98.7%.

As stated above, the superiority of the process of the invention over the prior art is based, in particular, on the demonstration of the kinetics of saponification of the (E) and (Z) isomers of the 2-propyl-2-pentenoic esters of formula I.

BRIEF DESCRIPTION OF DRAWING

This difference in kinetics is clearly visible in the attached FIGURE. This FIGURE shows, by way of example:

the curves for the kinetics of saponification of (E) (curve a) and (Z) (curve b) isomers of ethyl 2-propyl-2-pentenoate by means of 5 equivalents of sodium hydroxide at 40° C. and in a water/ethanol medium the curve for the kinetics of formation of the corresponding mixture of sodium salts containing sodium salts of the (E) and (Z) isomers of 2-propyl-2-pentenoic acid and of the $\Delta^3$ isomer (curve c).

Thus, by limiting the saponification reaction to a degree of conversion in the region of 90%, it is possible to reduce by one half the percentage of (Z) isomer contained in the crude 2-propyl-2-pentenoic acid relative to the (Z) isomer contained in the 2-propyl-2-pentenoic ester of formula I, without increasing the level of $\Delta^3$ isomer.

The pharmaceutically acceptable salts of (E)-2-propyl-2-pentenoic acid can, for their part, be obtained by reaction, in a suitable solvent such as toluene, with a suitable basic agent, for example an alkali metal hydroxide such as sodium hydroxide or an alkali metal carbonate such as sodium carbonate, to form a pharmaceutically acceptable salt, preferably the sodium salt.

The non-limiting examples which follow illustrate the compositions of the invention and also their use:

EXAMPLE 1

Preparation of a composition consisting of a mixture of (E) and (Z) isomers of ethyl 2-propyl-2-pentenoate.

a) Preparation of ethyl 2-bromo-2-propylpentanoate 144 g of 2-propylpentanoic acid and 0.5 g of N,N-dimethylformamide are introduced under a nitrogen atmosphere into a Grignard reactor.

The mixture is heated to 65° C., and 128.4 g of thionyl chloride are added in the course of 8 h while the temperature of the medium is maintained at between 65° and 70° C. When the addition is complete, the medium is heated to 95° C. and this temperature is maintained for one hour. 40 g of 1,2-dichloroethane are then introduced, the mixture is heated to 100° C., and 164 g of bromine are added in the course of 8 h. The temperature of the medium is maintained at 110°-115° C. for one hour after the addition is complete, the reaction mixture is cooled to 80°-85° C., and 74 g of absolute ethanol are then added in the course of 2 h 30 min. The mixture is heated to reflux for one hour and then cooled to 20° C. before adding 40 g of water. Settling is allowed to take place, the organic phase is concentrated and the oily residue is distilled [B.p.: 117°-119° C. (20 mmHg)].

In this manner, 242 9 of ethyl 2-bromo-2-propylpentanoate are obtained. Yield: 96.5%.

b) Preparation of a mixture of (E) and (Z) isomers of ethyl 2-propyl-2-pentenoate 0.43 mol of amine, 320 ml of N,N-dimethylformamide and 53 g (0.21 mol) of ethyl 2-bromo-2-propylpentanoate are introduced into a 500-ml Grignard reactor. The reaction medium is heated to a temperature T for X hours. The mixture is then cooled to 20° C. and 100 ml of water are added, followed by 50 ml of concentrated hydrochloric acid. The medium is left stirring for 1 hour and then extracted with 3 times 400 ml of hexane. The organic phases are washed with 3 times 350 ml of water, dried over sodium sulphate and concentrated.

In this manner, a mixture of (E) and (Z) isomers of ethyl 2-propyl-2-pentenoate is obtained in the form of a colourless oily residue free from ethyl 2-propyl-3-pentenoate.

Using the process described above, the following results were obtained:

| Amine | T (°C.) | X (h) | Gross Yield (%) | Ratio of isomers, E/Z* |
|---|---|---|---|---|
| DABCO | 55 | 21 | 96.7 (35 g) | 89:11 |
| DABCO | 90 | 4.5 | 97 | 86:14 |

Using the same process as that described above, but heating the reaction medium to a temperature $T_1$ for $X_1$ hours and then to a temperature $T_2$ for $X_2$ hours, the following results were obtained:

| Amine | $T_1$ (°C.) $T_2$ (°C.) | $X_1$ (h) $X_2$ (h) | Gross Yield (%) | Ratio of isomers, E/Z* |
|---|---|---|---|---|
| TMA | 55 | 44 | | 89:11 |
|  | 80 | 4 | 89 |  |
| TEA | 55 | 16 |  | 88:12 |
|  | 100 | 22 | 91 |  |
| TMEDA | 55 | 17 |  | 85:15 |
|  | 100 | 9 | 90 |  |

*Determined by nuclear magnetic resonance (NMR) in CDCl$_3$ (300 MHz): triplet at 6.75 and 5.80 ppm.

EXAMPLE 2

Preparation of a composition consisting of a mixture of (E) and (Z) isomers of ethyl 2-propyl-2-pentenoate.

Following the same working process as that described in Example 1, 100 g of ethyl 2-bromo-2-propylpentanoate are completely converted in 200 ml of N,N-dimethylformamide without the addition of a tertiary amine, the reaction being carried out at 125° C. for 15 hours.

In this manner, a mixture of (E) and (Z) isomers of ethyl 2-propyl-2-pentenoate is obtained in an E/Z ratio of 85:15.

EXAMPLE 3

Preparation of (E)-2-propyl-2-pentenoic acid a) Saponification 20.4 ml of water, 12 g of sodium hydroxide pellets and 20.4 ml of ethanol are introduced under argon into a Grignard reactor. The mixture is heated to 40° C. and 10.21 g (0.06 mol) of a 90:10 mixture of (E)/(Z) isomers of ethyl 2-propyl-2-pentenoate are added rapidly. The reaction medium is maintained at this temperature for 130 minutes. The conversion of ester to acid is then approximately 90% (check by gas chromatography). 100 ml of purified water and 30 ml of diisopropyl ether are added to the reaction medium. Settling is allowed to take place and the aqueous phase is extracted once more with 30 ml of diisopropyl ether. The aqueous phase is acidified with 35 ml of 37% hydrochloric acid and extracted with 3 times 50 ml of diisopropyl ether. The organic phases are combined and washed with 3 times 50 ml of water. The combined organic extracts are dried over sodium sulphate and concentrated in a rotary evaporator (temperature $\leq 30+$ C.).

In this manner, 7.7 g of (E)-2-propyl-2-pentenoic acid are obtained. Yield: 90.3%.

By NMR in CDCl$_3$ (300 MHz), the E/Z isomer ratio is determined, =94:6 (triplet at 6.8 and 6 ppm).

b) Isolation of (E)-2-propyl-2-pentenoic acid 22 ml of ethanol, 33 ml of water and 7.6 g of (E)-2-propyl-2-pentenoic acid obtained above are introduced into a 100-ml three-necked round-bottomed flask. The medium is heated to reflux and then cooled, slowly in the course of 1 hour, from 30° C. to −10° C. (E)-2-Propyl-2-pentenoic acid precipitates at about 0° C. After filtration, the precipitate obtained is recrystallised under the same conditions and then made into a paste again with a 70:30 water/ethanol mixture.

In this manner, 6.5 g of (E)-2-propyl-2-pentenoic acid are obtained.

Yield relative to ethyl (E)-2-propyl-2-pentenoate: 85.5%

Yield relative to ethyl 2-bromopentanoate: 74.2%

Purity determined by capillary gas chromatography (GC): titer 98.9% of (E) isomer M.p.: 38° C.

Impurities: (Z) isomer: 0.7% $\Delta^3$ isomer: 0.4%

EXAMPLE 4

Preparation of (E)-2-propyl-2-pentenoic acid a) Saponification

A Grignard reactor is charged at a temperature of 20° C. with 1.0 kg (5.88 mol) of an 87:13 mixture of (E)/(Z) isomers of ethyl 2-propyl-2-pentenoate (b.p. 75° C. at 10 mm Hg; d=0.92 at 20° C.; yield: 97% relative to ethyl 2-bromo-2-propylpentanoate), 0.48 kg (607 ml) of ethanol, 0.6 kg (600 ml) of water and 0.271 kg (6.775 mol) of sodium hydroxide flakes. The mixture is brought to manifest reflux during 1 hour and maintained thereat for 1 hour. It is cooled to 20° C., and 0.817 kg (8.06 mol) of 36% hydrochloric acid is introduced in the course of 1 hour while cooling is continued to about 0° C. The mixture is kept stirring at 0° C. for 1 hour and is then cooled to −10° C. for 1 hour. The precipitate is drained and rinsed, first by means of a mixture, chilled to −10° C., composed of 0.33 kg of ethanol and 0.84 kg of water, and then by means of 1.2 kg of water chilled to 0° to 5° C.

The product is then dried at 20° C. under vacuum or in a ventilated oven.

In this manner, 0.650 kg of (E)-2-propyl-2-pentenoic acid is obtained in the form of a clear, colourless liquid.

Yield: 89.6% relative to ethyl (E)-2-propyl-2-pentenoate, or 75.6% relative to ethyl 2-bromo-2-propylpentanoate.

Purity determined by GC: titer 96% of (E) isomer

Impurities: (Z) isomer: 2.8% $\Delta^3$ isomer: 1.1% b) Isolation of (E)-2-propyl-2-pentenoic acid

In a Grignard reactor, 0.650 kg of (E)-2-propyl-2-pentenoic acid, obtained above, is dissolved at 70° C. in a mixture of 0.75 kg (950 ml) of ethanol and 0.95 kg (950 ml) of water. The mixture is cooled to 0° C. and maintained for 1 hour at this temperature. It is cooled to −10° C. for 1 hour and the product is drained and rinsed by means of a mixture composed of 0.155 kg (196 ml) of ethanol and 0.2 kg (200 ml) of purified water, the mixture being chilled beforehand to −10° C.

The product is then dried at 20° C. under vacuum or in a ventilated oven.

In this manner, 0.580 kg of (E)-2-propyl-2-pentenoic acid is collected in the form of a white, crystalline powder.

Purification yield: 89%, corresponding to an 80% yield relative to ethyl (E)-2-propyl-2-pentenoate, or a 67% yield relative to ethyl 2-bromo-2-propylpentanoate.

Purity determined by GC: titer 99.6% of (E) isomer

Impurities: (Z) isomer: 0.2%

| Impurities: | (Z) isomer: 0.2% |
|---|---|
| | : 0.2% (artefact) |

EXAMPLE 5

Preparation of (E)-2-propyl-2-pentenoic acid a) Saponification

Using the same process as Example 4a, starting from 1.0 kg (5.88 mol) of an 88:12 mixture of (E)/(Z) isomers of ethyl 2-propyl-2-pentenoate (yield: 96% relative to ethyl 2-bromo-2-propylpentanoate), 0.660 kg of (E)-2-propyl-2-pentenoic acid is obtained. Yield: 90% relative to ethyl (E)-2-propyl-2-pentenoic, or 76% relative to ethyl 2-bromo-2-propylpentanoate.

b) Isolation of (E)-2-propyl-2-pentenoic acid

Using the same process in Example 4b, 0.620 kg of (E)-2-propyl-2-pentenoic acid is isolated.

Purification yield: 94%, corresponding to an 84.4% yield relative to ethyl (E)-2-propyl-2-pentenoate, or a 71.5% yield relative to ethyl 2-bromo-2-propylpentanoate.

Purity determined by GC: titer 99.8% of (E) isomer

| Impurities: | (Z) isomer: 0.01% |
|---|---|
| | : 0.01% (artefact) |

We claim:

1. Composition consisting of a mixture of (E) and (Z) isomers of esters of general formula:

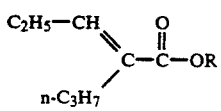

in which R represents a $C_1$–$C_4$ alkyl radical, containing at least 85% of (E) isomer.

2. Composition according to claim 1, containing 90% of (E) isomer.

3. Composition according to claim 1, wherein R represents an ethyl radical.

4. Process for preparing a composition according to claim 1, wherein the following steps are carried out: an α-bromo ester of general formula:

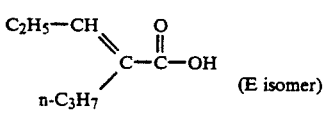

in which R has the same meaning as in claim 1, is heated to a temperature of 30° C. to 130° C. in a polar aprotic solvent containing an amide group, and optionally in the presence of a tertiary amine, yielding the desired composition.

5. Process for preparing (E)-2-propyl-2-pentenoic acid of formula:

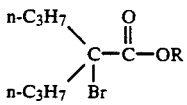

or a pharmaceutically acceptable salt thereof, wherein a composition according to claim 1 is saponified by means of an alkali metal hydroxide in an aqueous reaction medium containing an alcohol of general formula:

R—OH    III in which R has the same meaning as above, then acidifying the medium by means of a strong acid to obtain essentially the desired (E)-2-propyl-2-pentenoic acid.

6. Process for preparing (E)-2-propyl-2-pentenoic acid of formula:

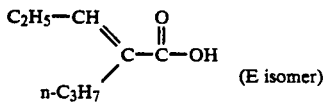

(E isomer)

or a pharmaceutically acceptable salt thereof, wherein: a mixture of (E) and (Z) isomers, containing at least 85% of (E) isomer, of esters of general formula:

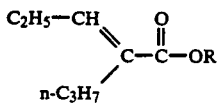

in which R represents a $C_1$–$C_4$ alkyl radical, is saponified to a degree of conversion of 90 to 92% by means of an alkali metal hydroxide in a reaction medium containing an alcohol of general formula:

 III in which R has the same meaning as above, the unsaponified esters are extracted by means of water-immiscible solvent and the aqueous reaction medium is acidified by means of a strong acide after extraction of the unsaponified esters, to obtain essentially the desired (E)-2-propyl-2-pentenoic acid.

7. Process for preparing (E)-2-propyl-2-pentenoic acid of formula:

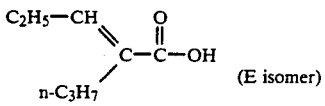

(E isomer)

or a pharmaceutically acceptable salt thereof, wherein:
a) an α-bromo ester of general formula:

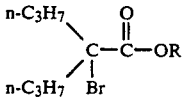

in which R represents a $C_1$–$C_4$ alkyl radical, is heated to a temperature of 30° C. to 130° C. in a polar aprotic solvent containing an amide group, and optionally in the presence of a tertiary amine, yielding a composition consisting of a mixture of (E) and (Z) isomers of esters of general formula:

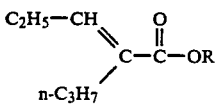

in which R represents a $C_1$–$C_4$ alkyl radical, the mixture containing at least 85% of (E) isomer
b) the composition thereby obtained is saponified by means of a alkali metal hydroxide in an aqueous reaction medium containing an alcohol of general formula:

 III in which R has the same meaning as above, and the medium is then acidified by means of a strong acid to obtain essentially the desired (E)-2-propyl-2-pentenoic acid.

8. Process according to claim 5 wherein the (E)-2-propyl-2-pentenoic acid is further purified by one or more crystallisations in an aqueous medium containing an alcohol of formula III, yielding (E)-2-propyl-2-pentenoic acid in pure form.

9. Process according to claim 8, wherein the purification is performed in an aqueous medium containing 50 to 150% by volume of an alcohol of formula III.

10. Process according to claim 4, wherein the α-bromo ester of formula IV is heated to a temperature of 100° to 125° C. in a polar aprotic solvent containing an amide group.

11. Process according to claim 4, wherein the α-bromo ester of formula IV is heated to a temperature of 30° to 100° C. in a polar aprotic solvent containing an amide group, and in the presence of a tertiary amine.

12. Process according to claim 4, wherein the polar aprotic solvent containing an amide group is N,N-dimethylformamide, N,N-dimethylacetamide or N-methylpyrrolidone.

13. Process according to claim 4, wherein a maximum of 2 mol of tertiary amine are used per mole of α-bromo ester of formula IV.

14. Process according to claim 4, wherein the tertiary amine is a $C_1$–$C_4$ trialkylamine.

15. Process according to claim 4, wherein the tertiary amine is trimethylamine, triethylamine or trimethylethylenediamine.

16. Process according to claim 4, wherein the tertiary amine is 1,4-diazabicyclo[2.2.2]octane.

17. Process according to claim 4, wherein the α-bromo ester of formula IV is ethyl 2-bromo-2-propylpentanoate.

18. Process according to claim 7, wherein the saponification takes place at a temperature ranging from room temperature to 100° C.

19. Process according to claim 7, wherein the saponification is performed by means of 1 to 10 equivalents of alkali metal hydroxide.

20. Process according to claim 7, wherein the alkali metal hydroxide is sodium hydroxide.

21. Process according to claim 7, wherein the aqueous reaction medium contains 50 to 150% by volume of an alcohol of formula III.

22. Process according to claim 7, wherein the acidification takes place at a temperature of +20° C. to −10° C.

23. Process according to claim 7, wherein the strong acid is hydrochloric acid.

24. Process according to claim 7, wherein (E)-2-propyl-2-pentenoic acid is reacted with an alkali metal hydroxide or an alkali metal carbonate to obtain a pharmaceutically acceptable salt.

25. Composition according to claim 2, wherein R represents an ethyl radical.

26. Process according to claim 7, wherein the α-bromo ester of formula IV is heated to a temperature of 100° to 125° C. in a polar aprotic solvent containing an amide group.

27. Process according to claim 7, wherein the α-bromo ester of formula IV is heated to a temperature of 30° to 100° C. in a polar aprotic solvent containing an amide group, and in the presence of a tertiary amine.

28. Process according to claim 7, wherein the polar aprotic solvent containing an amide group is N,N-dimethylformamide, N,N-dimethylacetamide or N-methylpyrrolidone.

29. Process according to claim 7, wherein a maximum of 2 mol of tertiary amine are used per mole of α-bromo ester of formula IV.

30. Process according to claim 7, wherein the tertiary amine is a $C_1$–$C_4$ trialkylamine.

31. Process according to claim 7, wherein the tertiary amine is trimethylamine, triethylamine or trimethylethylenediamine.

32. Process according to claim 7, wherein the tertiary amine is 1,4-diazabicyclo[2.2.2]octane.

33. Process according to claim 7, wherein the α-bromo ester of formula IV is ethyl 2-bromo-2-propylpentanoate.

34. An ester of the formula:

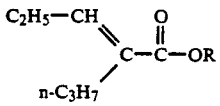   I wherein R is a $C_1$–$C_4$ alkyl radical, consisting of a mixture of (E) and (Z) isomers comprised of at least 85% of the (E) isomer.

35. The ester of claim 34 wherein the (E) isomer comprises at least 90% of the mixture.

36. The ester of claim 34 wherein the (E) isomer comprises 90% of the mixture.

37. The ester of claim 34 wherein R is ethyl.

* * * * *